United States Patent [19]
Mahoney

[11] 3,965,149
[45] June 22, 1976

[54] METHOD FOR RECOVERY OF METHYL METHACRYLATE FROM MIXED POLYMERIC MATERIALS

[75] Inventor: Lee R. Mahoney, Livonia, Mich.

[73] Assignee: Ford Motor Company, Dearborn, Mich.

[22] Filed: Nov. 4, 1974

[21] Appl. No.: 520,760

Related U.S. Application Data

[62] Division of Ser. No. 413,279, Nov. 5, 1973.

[52] U.S. Cl. ............................................. 260/486 R
[51] Int. Cl.² ........................................ C07C 69/54
[58] Field of Search ............................... 260/486 R

[56] References Cited
UNITED STATES PATENTS

| | | | |
|---|---|---|---|
| 2,030,901 | 2/1936 | Strain | 260/486 R |
| 2,341,282 | 2/1944 | Marks | 260/486 R |
| 2,377,952 | 6/1945 | Marks | 260/486 R |

Primary Examiner—Lorraine A. Weinberger
Assistant Examiner—P. J. Killos
Attorney, Agent, or Firm—Olin B. Johnson; Keith L. Zerschling

[57] ABSTRACT

A method for recovering methyl methacrylate from a mixture of polymeric materials containing poly (methyl methacrylate) which comprises contacting the mixture with a boiling $C_5 - C_8$ alkane, separating an insoluble residue containing poly (methyl methacrylate) from the alkane and its extract, extracting poly (methyl methacrylate) from such insoluble residue with boiling acetone, separating the poly (methyl methacrylate) from the acetone, and recovering the methyl methacrylate monomer from such poly (methyl methacrylate) by pyrolysis. In a preferred embodiment, the poly (methyl methacrylate) containing solid obtained after the acetone extraction is compressed under elevated temperatures and pressures prior to pyrolysis. The method can be stopped prior to the pyrolysis step when it is desired to recover only the poly (methyl methacrylate).

4 Claims, No Drawings

METHOD FOR RECOVERY OF METHYL METHACRYLATE FROM MIXED POLYMERIC MATERIALS

This is a division of application Ser. No. 413,279, filed Nov. 5, 1973.

BACKGROUND OF THE INVENTION

Increased use of synthetic organic polymeric materials commonly referred to as "plastics" in automobile and other industrial production is creating a growing disposal problem. The present method of most common use for disposal of non-metallic components of the product from automobile shredders is by sanitary land fill. Aside from the complete loss of the value of such materials by such disposal, the increasing volume of such scrap and the cost and availability of nearby land fill sites will soon create a major disposal problem. Further, current and potential shortages of some of the monomeric materials used to form such polymeric materials provides a compelling reason to recover and reuse such materials wherever feasible.

One such material used in large quantities is poly (methyl methacrylate), hereinafter called PMMA. A large and increasing quantity of PMMA is a product of automobile shredders which now have as their primary function the recovery of metal from junked automobiles for recycling. The total product of such shredders is commonly subjected to magnetic separation techniques leaving the non-ferrous metals and the plastics in a non-magnetic fraction.

Analysis of a 8.3 lb. sample of the non-magnetic fraction from conventional shredding of an automobile manufactured in the United States, i.e., a sample with density between 1.2 and 1.16 grams/cm$^3$ and particle size larger than 0.185 inch and smaller than 1.0 inch in diameter revealed the following composition:

Table I

| Material | % Composition |
|---|---|
| PMMA | 30.2 |
| Rubber | 7.8 |
| Assorted Plastics | 6.2 |
| Fabric (polyvinyl chloride) | 1.9 |
| Metal | 2.7 |
| Poly (vinyl butyral) | 0.6 |
| Glass | 0.9 |
| Tar and dirt | 49.7 |

THE INVENTION

Methyl methacrylate monomer, hereinafter called MMA, of relatively high purity can be quantitatively recovered from the non-magnetic fraction of automobile scrap containing PMMA by a process comprising in the following sequence (1) a first extraction step wherein the combined plastic scrap containing particulate PMMA is subjected to extraction with a boiling $C_5$ – $C_8$ alkane or a mixture of $C_5$ – $C_8$ alkanes, (2) the insoluble residue of the alkane extraction step is subjected to extraction with boiling acetone, and (3) separation of the acetone from the acetone extract and pyrolysis of the resulting solid residue at a temperature in the range of about 250° to about 500°C.

It will be understood by those skilled in the art that the process may be stopped after the separation of the acetone extract if desired or that the PMMA may be recovered by one processer and later pyrolyzed by another to recover MMA.

For efficient and quantitative recovery of the methyl methacrylate, the mixed plastic material is particulated by shredding or grinding to an average maximum particle diameter not exceeding one-half inch, preferably not exceeding about one-sixteenth inch.

After the acetone extraction and separation of the acetone from the PMMA comprising extract, the PMMA purity of the extract is further enhanced by compression molding the solid extract at a temperature in the range of 325°F. to 390°F. and at a pressure in the range of 3,000 psi to 50,000 psi for a time in excess of 1 minute, e.g., 1 to 5 minutes. Pyrolysis of the thus compressed extract will then yield methyl methacrylate monomer of additional purity.

The contact of the boiling hydrocarbon with the mixed particulate plastic is not critical as to time but is advisedly in excess of 1 minute and preferably in excess of 30 minutes, e.g., about 0.5 to about 20 hours. The time of contact between the boiling acetone and the insoluble residue from the first extraction step will determine the degree of PMMA extraction. Such contact will be in the range of 0.5 to 20 hours, advisedly in the range of 5 to 15 hours.

The pyrolysis of poly (methyl methacrylate) is discussed at pages 173–193 in Thermal Degradation of Organic Polymers by S. L. Madorsky, Interscience Publishers, John Wiley & Sons Inc., New York, New York (1964) and the teachings therein are incorporated herein by reference.

This invention will be more easily understood from the following illustrative examples.

Example 1

A 953.3 gram portion of the shredded mixture of Table I is placed in boiling n-hexane, i.e., about 68.7°C., in a soxhlet extraction apparatus which provides for continuous circulation of the extractant and collection of the extract for about 16 hours. The hexane and hexane extract upon separation leaves an insoluble residue. This insoluble residue in the amount of about 824 grams is shaken on a 16 mesh screen and about 96 grams of fine material pass through the screen. The material remaining on the screen weighs about 728 grams. This material is then placed in boiling acetone, i.e., about 56.5°C., in a soxhlet extraction apparatus which provides for continuous circulation of the extractant and collection of the extract for about 16 hours. The acetone and acetone extract (1000 ml) is separated from the insoluble residue and the acetone extract is evaporated to dryness. The solid residue remaining after such evaporation is vacuum dried at 80°C. and 10 mm Hg. pressure to yield 230.6 grams of a red solid. This red solid is placed in an evacuated closed reactor, i.e., a reactor wherein the pressure is maintained at about 0.1 mm Hg., and heated to a temperature of 400°C. until complete pyrolysis of the PMMA results. The gaseous effluent from the reactor is condensed by being passed through a cold trap maintained at – 70°C., i.e., through a conduit immersed in a solid carbon dioxide - acetone slurry coolant, and collected in liquid form. Analysis of this material by gas chromatography reveals that it contains 95.5 percent by weight methyl methacrylate. Compression molding of a portion of the red solid material at a temperature of 370°F. and a pressure of 30,000 psi for 5 minutes yields a homogeneous disc with a smooth, non-oil surface. Analysis of this molded material by pyrolytic gas chromotography reveals that it contains 98.0 percent by weight PMMA.

A comparison test is carried out to determine the value of the hydrocarbon extraction step. A 91.2 gram sample of the material from Table I is extracted with boiling acetone for 16 hours in a soxhlet extraction apparatus using all of the same conditions used before but without previous hexane extraction. The acetone extract (300 ml) is evaporated to dryness to yield 40.3 grams of a dark red solid. This solid is too viscous to be screened. Analysis of this solid by gel permeation chromatography reveals that it contains 73.6 percent by weight PMMA of approximate molecular weight 100,000 to 150,000 units. Further vacuum drying at 60°C. and 10 mm Hg. pressure yields a material which upon analysis by pyrolytic gas chromatography is revealed to contain 88.9 percent by weight PMMA.

Example 2

The procedure of Example 1 is repeated except for the fact that the pyrolysis of the PMMA is carried out under a $N_2$ atmosphere and the gaseous effluent of the pyrolysis is cooled with an ice water bath.

Example 3

The procedure of Example 1 is repeated except for the fact that boiling petroleum ether, i.e., an isomeric mixture pentanes, is substituted for the boiling n-hexane and the particulate mixture of polymeric materials is subjected to such extraction for 0.5 hour prior to the acetone extraction step.

Example 4

The procedure of Example 1 is repeated except for the fact that boiling n-octane is substituted for the boiling n-hexane.

Example 5

The procedure of Example 1 is repeated except for the difference that the compression of the solid of the acetone extract is carried out at a temperature of 390°F. and a pressure of 10,000 psia for 5 minutes prior to pyrolysis.

Example 6

The procedure of Example 1 is repeated except for the difference that the compression of the solid of the acetone extract is carried out at a temperature of 390°F. and a pressure of 25,000 psia for 1 minute prior to pyrolysis.

Example 7

The procedure of Example 1 is repeated except for the difference that the pyrolysis of the PMMA comprising solid from the acetone extraction step is carried out at 250°C.

EXAMPLE 8

The procedure of Example 1 is repeated except for the difference that the pyrolysis of the PMMA comprising solid from the acetone extraction step is carried out at 350°C.

Example 9

The procedure of Example 1 is repeated except for the difference that the pyrolysis of the PMMA comprising solid from the acetone extraction step is carried out at 500°C.

It will be understood by those skilled in the art that the foregoing examples are illustrative and that modifications thereof can be made within the scope of the invention as set forth in the appended claims.

I claim:
1. A method for recovering methyl methacrylate monomer from a particulate mixture of polymeric materials containing poly (methyl methacrylate) which comprises in combination:
    1. subjecting said particulate mixture of polymeric materials to continuous extraction with a boiling $C_5 - C_8$ alkane for a time in excess of 1 minute.
    2. separating the alkane from a resultant insoluble residue of said particulate mixture of polymeric materials,
    3. subjecting said insoluble residue to continuous extraction with boiling acetone for a time in the range of about 0.5 to about 20 hous,
    4. separating the acetone and resultant acetone extract from a resultant insoluble residue of said particulate mixture of polymeric materials,
    5. volatilizing acetone from the acetone extract leaving a poly (methyl methacrylate)-comprising solid,
    6. pyrolysis of said poly (methyl methacrylate)-comprising solid at a temperature in the range of about 250° C. to about 500°C., and
    7. recovering methyl methacrylate monomer from said pyrolysis.

2. The method of claim 1 wherein said poly (methyl methacrylate)-comprising solid is compressed under a pressure in the range of about 3,000 to about 50,000 psi and at a temperature in the range of about 325° to about 390°F. for a time in excess of 1 minute prior to said pyrolysis.

3. The method of claim 1 wherein said continuous extraction with boiling $C_5 - C_8$ alkane of said particulate mixture of polymeric materials is for a time in the range of about 0.5 to about 20 hours.

4. The method of claim 1 wherein said pyrolysis of said poly (methyl methacrylate) is carried out under sub-atmospheric pressure and methyl methacrylate monomer is recovered by liquidification of gases generated in said pyrolysis.

\* \* \* \* \*